United States Patent [19]

Juneja

[11] Patent Number: 5,284,649
[45] Date of Patent: Feb. 8, 1994

[54] DEODORANT GEL STICKS CONTAINING 1-HYDROXY PYRIDINETHIONE ACTIVE

[75] Inventor: Prem S. Juneja, Cincinnati, Ohio

[73] Assignee: The Procter & Gamble Company, Cincinnati, Ohio

[21] Appl. No.: 953,635

[22] Filed: Sep. 29, 1992

[51] Int. Cl.$^5$ .......................... A61K 7/32; A61K 7/36
[52] U.S. Cl. ............................. 424/67; 424/DIG. 5; 514/188; 514/852
[58] Field of Search .................. 514/852, 188; 424/65, 424/DIG. 5, 67

[56] References Cited

U.S. PATENT DOCUMENTS

| | | | |
|---|---|---|---|
| 2,732,327 | 1/1956 | Teller | 424/68 |
| 2,857,315 | 10/1958 | Teller | 424/68 |
| 2,900,306 | 8/1959 | Slater | 424/68 |
| 2,970,083 | 1/1961 | Bell | 424/68 |
| 3,412,033 | 11/1968 | Karsten et al. | 252/107 |
| 3,636,213 | 1/1972 | Gerstein et al. | 514/852 |
| 3,852,441 | 12/1974 | Kooistra | 424/245 |
| 3,862,305 | 1/1975 | Bouillon et al. | 424/45 |
| 3,917,815 | 11/1975 | Kalopissis et al. | 424/45 |
| 3,940,482 | 2/1976 | Grand | 514/852 |
| 3,966,928 | 6/1976 | Douglass | 424/65 |
| 3,969,087 | 7/1976 | Saito et al. | 44/7 |
| 4,041,033 | 8/1977 | Douglass | 424/65 |
| 4,049,792 | 9/1977 | Elsnau | 424/66 |
| 4,154,816 | 5/1979 | Roehl et al. | 424/68 |
| 4,235,873 | 11/1980 | Packman | 424/47 |
| 4,323,683 | 4/1982 | Bolich et al. | 546/6 |
| 4,345,080 | 8/1982 | Bolich | 546/6 |
| 4,457,938 | 7/1984 | Bittera et al. | 424/DIG. 5 |
| 4,504,465 | 3/1985 | Sampson et al. | 424/DIG. 5 |
| 4,518,582 | 5/1985 | Schamper et al. | 424/66 |
| 4,743,444 | 5/1988 | McCall | 424/65 |
| 4,759,924 | 7/1988 | Luebbe et al. | 424/42 |
| 4,816,261 | 3/1989 | Luebbe et al. | 424/65 |
| 4,906,454 | 3/1990 | Melanson et al. | 514/852 |

FOREIGN PATENT DOCUMENTS

| | | | |
|---|---|---|---|
| 1164347 | 3/1984 | Canada | 424/68 |
| 107330 | 5/1984 | European Pat. Off. | 424/65 |
| 117070 | 8/1984 | European Pat. Off. | 424/66 |
| 60-23309 | 2/1985 | Japan | 424/868 |
| 1-207223 | 8/1989 | Japan | 424/DIG. 5 |
| 2-180805 | 7/1990 | Japan | 424/59 |

OTHER PUBLICATIONS

Sagarin, Cosmetics Science and Technology, (1957), Interscience Publishers, Inc. New York, pp. 717 & 731-737.

*Primary Examiner*—Dale R. Ore
*Attorney, Agent, or Firm*—Steven J. Goldstein; Leonard W. Lewis

[57] ABSTRACT

Deodorant gel stick compositions, which are essentially free of water, comprising a heavy metal salt of 1-hydroxy pyridinethione as the deodorant active, a gelling agent, and a solvent system (preferably a polar solvent) are disclosed. These compositions have minimized component interactions, active component stability, and are excellent in the prevention of body malodors. Preferred compositions utilize zinc pyrithione as the deodorant active, and contain less than about 1% water. Other standard deodorant components may be included in compositions for cosmetic purposes.

20 Claims, No Drawings

DEODORANT GEL STICKS CONTAINING 1-HYDROXY PYRIDINETHIONE ACTIVE

TECHNICAL FIELD

The present invention relates to deodorant gel stick compositions. The compositions herein have excellent deodorant efficacy and minimized negative component interactions.

BACKGROUND OF THE INVENTION

Human body malodors are generally believed to be caused in part by microbial interaction with sweat gland secretions which produces pungent fatty acids. Aside from cleansing, one way such odors are controlled is by the use of deodorant products, particularly in the underarm area of the body.

Deodorant products generally consist of a safe and effective level of an antimicrobial active ingredient which is incorporated into a vehicle from which the active ingredient may be deposited on the skin. A deodorant product may be in on of several forms including, for example, liquids, solid wax sticks or gel sticks. The present invention relates to gel stick deodorant compositions.

Gel stick deodorant compositions have several advantages over other types of stick formulations. For example, they usually leave no more than a minimal amount of residue on the skin, and they glide easily over the skin when applied. Deodorant compositions of the gel stick type generally incorporate three key ingredients: a material known to have deodorant efficacy, a gelling agent, and a polar solvent system.

The gelling agents used most often in deodorant gel stick compositions ar of the fatty acid soap type. The gelling agents used in these compositions include, for instance, the sodium or potassium salts of $C_{12}$–$C_{18}$ fatty acids. Soap/alcohol gels which provide the benefits, discussed above, examples of which are disclosed in U.S. Pat. No. 2,732,327, Teller, issued Jan. 24, 1956; U.S. Pat. No. 2,857,315, Teller, issued Oct. 21, 1958; U.S. Pat. No. 2,900,306, Slater, issued Aug. 18, 1959, and U.S. Pat. No. 2,970,083, Bell, issued Jan. 31, 1961, have been available for quite some time. Other commercially available gelling agents which may be used include, for example, dibenzylidene monosorbitol acetal (known commercially as Millithix) and its analogs. Although useful as a gelling agent, Millithix has not been used extensively in deodorant gel stick compostions because water, which comprises as much as 25% of typical compositions, causes it to break down into its component parts, benzaldehyde and sorbitol, resulting in gel instability.

Several materials are known to have antimicrobial activity of the type that would be useful in a deodorant gel stick composition. Examples of such materials include the primary olamine salt of piroctone (known commercially as Octopirox), certain metal salts of piroctone acid (such as aluminum, sodium, potassium, zirconium, calcium and zinc metal salts), triclosan, zinc phenolsulfonate, and certain heavy metal salts of 1-hydroxy pyridinethione (such as zinc pyrithione, magnesium pyrithione, and aluminum pyrithione). The heavy metal salts of pyridinethione are active antimicrobials, bactericides, and fungicides. Certain of them are particularly adaptable to use on skin, hair, and textiles, as disclosed in U.S. Pat. No. 3,940,482, Grand, issued Feb. 24, 1976. For example, zinc pyrithione has been used for the control of dandruff, as disclosed in U.S. Pat. No. 4,345,080, Bolich, issued Aug. 17, 1982. The use of salts and derivatives of pyrithione and closely-related pyridine-N-oxide compounds in hair, skin or textile treating compositions is also taught in U.S. Pat. No. 3,412,033, Karsten, issued Nov. 19, 1968; U.S. Pat. No. 3,636,213, Gerstein, issued Jan. 18, 1972; U.S. Pat. No. 3,852,441, Kooistra, issued Dec. 3, 1974; U.S. Pat. No. 3,862,305, Bouillon, issued Jan. 21, 1975; U.S. Pat. No. 4,235,873, Packman, issued Nov. 25, 1980; and Japanese Published Application J60-23309, Lion, published Feb. 5, 1985.

Although known to have the necessary antimicrobial activity, the heavy metal salts of 1-hydroxy pyridinethione have not generally been used in deodorant gel stick applications. In the presence of the amounts of water typically found in gel sticks, such pyridinethione salts react with the soap gelling agents to form insoluble precipitates which result in a less desirable deodorant product. For example, when sodium stearate is used as the gelling agent in a gel stick where zinc pyrithione is the deodorant active, the level of water present in typical compositions (often greater than 20%) causes the formation of zinc stearate, which is ineffective, and sodium pyrithione, which is unacceptable.

U.S. Pat. No. 3,917,815, Kalopissis, issued Nov. 4, 1975, describes certain pyridine-N-oxide derivatives as actives for deodorancy in a conventional water-containing stearate-based gel stick. The compositions disclosed contain a significant amount of water. Additionally, the use of zinc pyrithione is not disclosed.

It is therefore an objective of the present invention to provide a deodorant gel stick composition, particularly a soap-based gel stick, in which heavy metal salts of 1-hydroxy pyridinethione are used as the deodorant active and the activity and integrity of the pyrithione salt are maintained.

It is a further objective of the present invention to provide a deodorant gel stick composition in which other water-sensitive components, such as dibenzylidene monosorbitol acetal gelling agent, may be effectively used without their breaking down into non-gelling and less desirable species (such as benzaldehyde).

All percentages and ratios used herein are by weight unless otherwise indicated.

SUMMARY OF THE INVENTION

The present invention provides a gel stick deodorant composition comprising:
(a) an effective amount of a heavy metal salt of 1-hydroxy pyridinethione as the antimicrobial deodorant active;
(b) from about 3% to about 20% of a gelling agent; and
(c) from about 1% to about 95% of a solvent system, preferably a polar solvent system.

All compositions herein are essentially free of water.

"Essentially free of water", as used herein, means that if water is included at all, the composition contains water at a level no greater than about 5%, preferably less than about 3%, and most preferably less than about 1% of the total composition.

"Stable", as used herein, means that the negative interactions of individual components in the deodorant composition which may result in substances which are either ineffective for their intended purpose or generally undesireable are eliminated or minimized. The stability of the present invention is achieved by ensuring that the amount of water present in the deodorant compositions is kept below a level at which such interactions are likely to take place to any significant extent.

"Effective amount" of deodorant active, as used herein, means that the deodorant active is included in the composition at a level sufficient to provide a level on the skin which results in the desired deodorancy/antimicrobial benefit without being so high as to cause skin irritation or raise other possible safety concerns.

DETAILED DESCRIPTION OF THE INVENTION

The components utilized in the present invention are described in detail below.

Antimicrobial Deodorant Active Ingredient

The antimicrobial deodorant actives useful in the present invention are the heavy metal salts of 1-hydroxy pyridinethione as, for example, those issued Apr. 6, 1982; and U.S. Pat. No. 4,345,080, Bolich, issued Aug. 17, 1982, both of which are incorporated herein by reference. These pyridinethione salts have the following structural formula in tautomeric form, the sulfur being attached at the 2-carbon position in the pyridine ring.

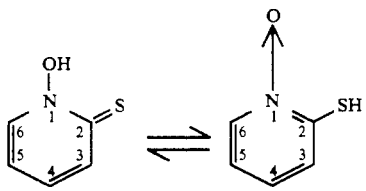

The metal salts represent substitution of the metal cation for the hydrogen of one of the tautomeric forms. Depending, of course, on the valence of the metal involved there may be more than one of the pyridinethione rings in the compound. Suitable heavy metal pyridinethione salts include, for example, the pyridinethione salts of zinc, tin, cadmium, and zirconium. The preferred heavy metal pyridinethione salt is zinc pyrithione (note that "pyrithione" and "pyridinethione" are used interchangeably, herein).

The heavy metal pyridinethione salt antimicrobial deodorant active is included in the compositions in an effective amount, typically from about 0.01% to about 0.25%, preferably from about 0.01% to about 0.10%, of the total composition. The more preferred level of heavy metal pyridinethione salt deodorant active is from about 0.02% to about 0.075%, most preferably from about 0.04% to about 0.06%, of the total composition.

Deodorant Gel Sticks

The deodorant compostions described in this invention are formulated as deodorant gel sticks. An essential component of such gel sticks is a gelling agent. Any gelling agent known for use in deodorant sticks may be used in the present invention. Examples of such gelling agents include soap-type gelling agents, dibenzylidene sorbitol-type gelling agents (see U.S. Pat. No. 4,154,816, Roehl et al., issued May 15, 1979; U.S. Pat. No. 4,816,26 Luebbe et al., issued Mar. 28, 1989; and U.S. Pat. No. 4,743,444, McCall, issued May 10, 1988, all incorporated herein by reference), N-acyl amino acids and derivatives thereof (see U.S. Pat. No. 4,969,087, Saito et al., issued Jul. 13, 1976; Japanese Published Application 1-207223, published Aug. 21, 1989; and Japanese Published Application 2-180805, published Jul. 13, 1990, all incorporated herein by reference), and 12-hydroxystearic acid (see Japanese Published Application 1-207223, published Aug. 21, 1989; and Japanese Published Application 2-180805, published Jul. 13, 1990, both incorporated herein by reference). Gel sticks utilizing soap type gelling agents are generally described in U.S. Pat. No. 2,857,315, Teller, issued Oct. 21, 1958, and U.S. Pat. No. 2,900,306, Slater, issued Aug. 18, 1959, both incorporated herein by reference. These sticks utilized soap as a gelling agent to form a firm gel matrix with good consumption characteristics. However, unlike the gel sticks disclosed therein, the present invention is essentially free of water and in any event does not include water at a level greater than about 5% of the total compositions.

Preferred gelling agents for use herein are the soap type gelling agents, such as sodium and potassium salts of fatty acids containing from about 12 to 18 carbon atoms, as disclosed in U.S. Pat. No. 4,759,924, Leubbe et al., issued Jul. 26, 1988, which is incorporated herein by reference. Preferred fatty acid soap type gelling agents include, for example, sodium stearate, sodium palmitate, potassium stearate, potassium palmitate, sodium myristate, and aluminum monostearate. Mixtures of soaps may also be used. The most preferred fatty acid soap type gelling agents are sodium stearate and potassium stearate, especially sodium stearate.

Also preferred as a gelling agent is dibenzylidene monosorbitol acetal (commercially available as Millithix from Milliken Chemicals), and analogs thereof. The fact that the compositions of the present invention are essentially free of water allows this gelling agent to be included without the stability problems which usually accompany its use.

These gelling agents generally comprise from about 3% to about 10%, preferably from about 5% to about 8%, and most preferably from about 5.5% to about 6%, of the composition.

Another essential component of the gel stick of the present invention is a solvent system which solubilizes the gelling agent, allowing the medium to gel. The solvent may also be used to solubilize the deodorant active. It is preferred that the solvents used herein be polar solvents. However, when gelling agents such as 12-hydroxy stearic acid or N-acyl amino acid derivatives are used, less polar solvents, such as volatile silicone oils (e.g., cyclomethicone) or $C_{12}$–$C_{15}$ alcohols benzoate (Finsolve) are generally used. The solvents are included in the compositions of the present invention at levels from about 7% to about 95%, preferably from about 30% to about 90%, most preferably from about 40% to about 80%, of the total composition. The solvent forms the base matrix of the solid stick when combined with the gelling agent. As will be appreciated by those skilled in the art, the selection of a particular solvent will depend upon the characteristics of the stick desired. For example, the solvent can be used to solubilize an antiperspirant active component if one is included. For another example, the solvent may be selected to provide such cosmetic benefits as emolliency when applied to the skin.

Polar solvents useful herein include, for example, lower monohydric alcohols, polyhydric alcohols, and mixtures thereof. Examples of solvents which may be utilized in the present invention include liquid polyethylene glycols (e.g., diethylene glycol, triethylene glycol), liquid polypropylene glycols (e.g., dipropylene glycol, tripropylene glycol), liquid polypropylene polyethylene glycol copolymers, ethanol, n-propanol, n-butanol, t-butanol, 2-methoxyethanol, 2-ethyoxyethanol, ethylene glycol, 1,2-propylene glycol, 1,3-propylene glycol, 1,4-butylene glycol, 1,2-butylene glycol, isopropanol, isobutanol, diethylene glycol monomethylether, diethylene glycol monoethylether, 1,3-butylene glycol, 2,3-butylene glycol, 2,4-dihydroxy-2-methylpentane, trimethylene glycol, glycerine, 1,3-butane diol, 1,4-butane diol, and the like, and mixtures thereof. As used herein, polyethylene glycols, polypropylene glycols, and polypropylene polyethylene glycol copolymers include alkyl ether derivatives of these compounds (e.g., ethyl, propyl, and butyl ether derivaties). Examples of such compounds are butyl ether derivatives of polypropylene polyethylene glycol copolymers, such as PPG-5-buteth-7. These solvents are fully described, for example, in U.S. Pat. No. 4,518,582, Schamper et al., issued May 21, 1985, and European published Application 107,330, Luebbe et al., published May 2, 1984, incorporated herein by reference.

Preferred polar solvents useful in the present invention include, for example, $C_2$–$C_9$ monohydric, dihydric, and polyhydric alcohols, propylene carbonate, 3-methyl-2-oxazolidinone, and ethyleneoxide polymers which are liquid at room temperature. Mixtures of polar solvents may also be used. Preferred examples of useful polyhydric alcohols for use herein include, for example, ethylene glycol, propylene glycol, dipropylene glycol, tripropylene glycol, trimethylene glycol, triethylene glycol, tetraethylene glycol, butylene glycol, hexylene glycol, PEG-400, glycerine, and mixtures thereof. Most preferred is dipropylene glycol.

Monohydric alcohols used herein not only provide solvency, but also provide certain cosmetic advantages such a cool feel to the skin and a strong scent which confirms the deodorant's presence to the user. Preferred monohydric alcohols include, for example, methanol, ethanol, isopropanol, and mixtures thereof; most preferred is ethanol.

Optional Components

Optional components useful in the present invention include a variety of ingredients which are conventionally used in solid deodorant compositions and which improve efficacy, processing, stability, cosmetics, and/or aesthetics of the final product. Such optional components include, for example, coupling agents, processing aids, dyes, pigments, coloring agents, emollients, humectants, hardeners, fillers, alcohol evaporation retardants, and perfumes. Optional components useful in the present invention are described in the following documents, all incorporated by reference herein: U.S. Pat. No. 4,049,792, Elsnau, issued Sep. 20, 1977; Canadian Patent 1,164,347, Beckmeyer et al., issued Mar. 27, 1984; European Patent Application 117,070, May, published Aug. 29, 1984; and Geria, "Formulation of Stick Antiperspirants an Deodorants", *Cosmetics & Toiletries*, 99:55–60 (1984).

Coupling agents, also known as emulsifiers, as used herein means any compound or component which acts to bring polar, intermediate polar, and non-polar components of the gel stick composition into a homogeneous mixture. Coupling agents useful in the present invention include, for example, polyethylene glycol (PEG), polypropylene glycol (PPG), and the PEG/PPG ethers of $C_4$–$C_{22}$ (preferably $C_{10}$–$C_{20}$) fatty alcohols; the most preferred is PPG-3 myristyl ether. It should be noted that some of these materials, particularly the PEG/PPG ethers of $C_4$–$C_{22}$ fatty alcohols, can serve both as solvents and coupling agents. When included, these coupling agents comprise from about 5% to about 60%, preferably from about 10% to about 50%, and most preferably from about 15% to about 30%, of the composition.

Dyes, pigments, and coloring agents may be used to achieve an aesthetically pleasing appearance for the product and reinforce the product's concept goals. The dyes, pigments, and coloring agents selected are those certified for use in drugs and cosmetic products. Such materials generally comprise from about 1 ppm to about 10 ppm of the finished composition.

An emollient may be included to provide lasting dry feel to the skin and reduce tackiness. These emollients are, for example, selected from the group consisting of volatile and nonvolatile silicones; fatty alcohols; esters formed by the reaction of $C_3$–$C_{18}$ fatty alcohols with $C_3$–$C_{18}$ fatty acids, such as di-isopropyl adipate, isopropyl myristate, isopropyl palmitate, glycerol monostearate, and $C_{12}$–$C_{15}$ alcohol lactates. Preferred emollients are the volatile silicones, such as cyclomethicone. The emollient, when used, comprises from about 10% to about 30% of the composition.

To prevent shrinkage of the stick resulting from the loss of alcohols, alcohol evaporation retardants may be included in the formula. These are generally polyhydric alcohols, such as glycerine, sorbitol, and mixtures thereof, and, when used, are included at levels of from about 1% to about 5% of the composition.

Method of Manufacture

Methods for making the deodorant gel sticks of the present invention are well-known to those skilled in the art. In general, a mixture of solvent, coupling agent, emollient, gelling agent, and deodorant active is heated while being vigorously agitated. This is continued until the gelling agent and deodorant active ar completely solubilized and the mixture is clear, which usually occurs at temperatures of from about 220° F. (104° C.) to about 275° F.(135° C.). The mixture is then cooled to a temperature of from about 150° F. (65° C.) to about 190° F. (88° C.), and the remainder of components, which may include, for example, dyes, pigments, and perfume, are added to the mixture under agitation. The composition is then poured into a mold and cooled to form the desired gel stick. It should be noted that while it is preferred that the deodorant active be included in the present invention in solubilized form, it may be included as a dispersion, provided the particle size of the material results in a cosmetically-acceptable product.

Method of Use

The deodorant compositions described herein are utilized in conventional ways to treat or prevent the development of malodors of the human body. Specifically, an effective amount of the deodorant compositions is applied topically to the skin, particularly the axillary areas, one or more times a day. When this is done, malodors are effectively prevented from developing.

EXAMPLE I

A deodorant gel stick of the present invention having the composition given below, and being essentially free of water, is prepared as follows.

| COMPONENT | % (BY WEIGHT) |
| --- | --- |
| dipropylene glycol | 39.85 |
| sodium stearate | 5.50 |
| PPG-3 myristyl ether | 29.40 |
| cyclomethicone-D5 | 21.00 |
| ethanol (200 proof) | 1.80 |
| perfume | 2.40 |
| zinc pyrithione (powder form-commercially available from Olin) | 0.05 |

All of the above materials, except the perfume, are vigorously mixed and heated to about 250° F. (121° C.), until the mixture is clear. The mixture is then cooled to about 175° F. (79° C.) and the perfume is added with stirring. The mixture is poured into stick molds and cooled to room temperature forming the deodorant gel stick compositions of the present invention.

EXAMPLE II

A deodorant gel stick of the present invention having the composition given below, and being essentially free of water, is prepared according to the method given in Example I.

| COMPONENT | % (BY WEIGHT) |
| --- | --- |
| dipropylene glycol | 51.95 |
| sodium stearate | 5.50 |
| PPG-3 myristyl ether | 25.33 |
| cyclomethicone-D5 | 13.33 |
| ethanol (200 proof) | 1.44 |
| perfume | 2.40 |
| zinc pyrithione (powder form) | 0.05 |

EXAMPLE III

A deodorant gel stick of the present invention having the composition given below, and being essentially free of water, is prepared according to the method given in Example I.

| COMPONENT | % (BY WEIGHT) |
| --- | --- |
| dipropylene glycol | 75.10 |
| sodium stearate | 5.50 |
| PPG-3 myristyl ether | 15.00 |
| ethanol (200 proof) | 1.95 |
| perfume | 2.40 |
| zinc pyrithione (25% water slurry) | 0.05 |

The deodorant products disclosed in Examples I–III are effective in preventing and treating body malodors. In addition, the components in these products, particularly the zinc pyrithione, remain stable and effective overtime.

What is claimed is:

1. A stable gel stick deodorant composition, essentially free of water, comprising:
   (a) an effective amount of a heavy metal salt of 1-hydroxy-pyridinethione as the deodorant active;
   (b) from about 3% to about 20% of a gelling agent selected from the group consisting of sodium and potassium salts of $C_{12}$–$C_{18}$ fatty acids, and mixtures thereof; and
   (c) from about 7% to about 95% of a polar solvent system.

2. A composition according to claim 1 wherein the deodorant active comprises from about 0.01% to about 0.25% of the composition.

3. A composition according to claim 2 wherein the deodorant active is zinc pyrithione.

4. A composition according to claim 3 wherein the deodorant active comprises from about 0.01% to about 0.10% of the composition.

5. A composition according to claim 4 wherein the deodorant active comprises from about 0.02% to about 0.075% of the composition.

6. A composition according to claim 2 wherein the gelling agent is selected from the group consisting of sodium stearate, potassium stearate, and mixtures thereof.

7. A composition according to claim 6 wherein the deodorant active is zinc pyrithione.

8. A composition according to claim 6 wherein the gelling agent is sodium stearate.

9. A composition according to claim 2 wherein the gelling agent comprises from about 5% to about 8% of the composition.

10. A composition according to claim 9 wherein the gelling agent comprises from about 5.5% to about 6% of the composition.

11. A composition according to claim 2 wherein the polar solvent system is selected from the group consisting of $C_2$–$C_9$ monohydric, dihydric, and polyhydric alcohols, propylene carbonate, 3-methyl-2-oxazolidinone, ethyleneoxide polymers which are liquid at room temperature, and mixture thereof.

12. A composition according to claim 11 wherein the polar solvent system is selected from the group consisting of ethanol, methanol, isopropanol, ethylene glycol, triethylene glycol, trimethylene glycol, tetraethylene glycol, propylene glycol, butylene glycol, hexylene glycol, dipropylene glycol, tripropylene glycol, glycerin, propylene carbonate, 3-methyl-2-oxazolidinone, PEG-400, and any mixture thereof.

13. A composition according to claim 12 wherein the deodorant active is zinc pyrithione.

14. A composition according to claim 12 wherein the polar solvent system is selected from the group consisting of dipropylene glycol, ethanol, and mixtures thereof.

15. A composition according to claim 14 wherein polar solvent system is dipropylene glycol.

16. A composition according to claim 14 wherein the polar solvent system comprises from about 30% to about 90% of the composition.

17. A composition according to claim 16 wherein the polar solvent system comprises from about 40% to about 80% of the composition.

18. A composition according to claim 11 wherein water comprises less than about 3% of the composition.

19. A composition according to claim 18 wherein water comprises less than about 1% of the composition.

20. A composition according to claim 18 comprising:
   (a) from about 0.02% to about 0.075% of zinc pyrithione;
   (b) from about 3% to about 10% of sodium stearate; and
   (c) from about 30% to about 90% of a polar solvent system selected from the group consisting of dipropylene glycol, ethanol and mixtures thereof.

* * * * *

UNITED STATES PATENT AND TRADEMARK OFFICE
CERTIFICATE OF CORRECTION

PATENT NO.  : 5,284,649

DATED       : February 8, 1994

INVENTOR(S) : Prem S. Juneja

It is certified that error appears in the above-identified patent and that said Letters Patent is hereby corrected as shown below:

Column 3, line 19 "for example, those issued" should read -- for example, those disclosed in U.S. Patent 4,323,683, Bolich et al., issued --.

Column 3, line 63 "U.S. Pat. No. 4,816,26." should read -- U.S. Pat. No. 4,816,261,--.

Signed and Sealed this

Second Day of August, 1994

*Attest:*

BRUCE LEHMAN

*Attesting Officer*    Commissioner of Patents and Trademarks